(12) United States Patent
Abu Shmeis et al.

(10) Patent No.: US 8,486,447 B2
(45) Date of Patent: Jul. 16, 2013

(54) PHARMACEUTICAL FORMULATION

(75) Inventors: Rama Ali Abu Shmeis, Arlington, MA (US); James Kowalski, Belle Mead, NJ (US); Steven L. Krill, Danbury, CT (US); Lakshman Jayanth Parthiban, Cedar Knolls, NJ (US); Zeren Wang, Southbury, CT (US)

(73) Assignee: Novartis AG, Basel (CH)

( * ) Notice: Subject to any disclaimer, the term of this patent is extended or adjusted under 35 U.S.C. 154(b) by 1611 days.

(21) Appl. No.: 10/543,289

(22) PCT Filed: Feb. 2, 2004

(86) PCT No.: PCT/EP2004/000925
§ 371 (c)(1),
(2), (4) Date: May 3, 2006

(87) PCT Pub. No.: WO2004/069138
PCT Pub. Date: Aug. 19, 2004

(65) Prior Publication Data
US 2006/0269608 A1 Nov. 30, 2006

Related U.S. Application Data

(60) Provisional application No. 60/444,602, filed on Feb. 3, 2003.

(51) Int. Cl.
*A61K 9/20* (2006.01)
(52) U.S. Cl.
USPC .......................................................... 424/464
(58) Field of Classification Search
None
See application file for complete search history.

(56) References Cited

U.S. PATENT DOCUMENTS

| | | | |
|---|---|---|---|
| 4,649,042 A * | 3/1987 | Davis et al. | 424/430 |
| 4,801,460 A * | 1/1989 | Goertz et al. | 514/772.5 |
| 5,072,379 A | 12/1991 | Eberhardt | |
| 5,340,591 A | 8/1994 | Nakano et al. | |
| 5,411,737 A * | 5/1995 | Hsu et al. | 424/411 |
| 5,456,923 A | 10/1995 | Nakamichi et al. | |
| 5,618,560 A * | 4/1997 | Bar-Shalom et al. | 424/486 |
| 5,620,697 A * | 4/1997 | Tormala et al. | 424/426 |
| 5,667,807 A | 9/1997 | Hürner et al. | |
| 5,707,655 A | 1/1998 | Kanikanti et al. | |
| 5,741,519 A | 4/1998 | Rosenberg et al. | |
| 5,792,474 A | 8/1998 | Rauchfuss | |
| 5,827,536 A | 10/1998 | Laruelle | |
| 6,187,342 B1 | 2/2001 | Zeidler et al. | |
| 6,197,349 B1 | 3/2001 | Westesen et al. | |
| 6,677,362 B1 | 1/2004 | Ghebre-Sellassie et al. | |
| 2001/0007678 A1 | 7/2001 | Baert et al. | |
| 2002/0012701 A1 | 1/2002 | Kolter et al. | |
| 2004/0013736 A1 | 1/2004 | Nakano et al. | |

FOREIGN PATENT DOCUMENTS

| | | |
|---|---|---|
| CA | 2322629 | 8/2000 |
| DE | 195 39 363 | 4/1997 |
| DE | 19539363 | 4/1997 |
| EP | 0043254 | 1/1982 |
| EP | 0 240 904 | 10/1987 |
| JP | 58079915 | 5/1983 |
| JP | A-05-139974 | 6/1993 |

OTHER PUBLICATIONS

Leuner C. et al., "Improving drug solubility for oral delivery using solid dispersions", European Journal of Pharmaceutics and Biopharmaceutics, (Elsevier Science Publishers B.V., Amsterdam, NL), vol. 50, No. 1, pp. 47-60, (Jul. 3, 2000).*
Aitken-Nichol Carolyn et al., "Hot melt extrusion of acrylic films", Pharmaceutical Research (New York), vol. 13, No. 5, pp. 804-808, (1996).
Forsters Angus et al., "Characterization of glass solutions of poorly water-soluble drugs produced by melt extrusion with hydrophilic amorphous polymers", Journal of Pharmacy and Pharmacology, vol. 53, No. 3, pp. 303-315, (Mar. 2001).
Usui F. et al., "Dissolution improvement of RS-8359 by the solid dispersion prepared by the solvent method", International Journal of Pharmaceutics (Amsterdam), vol. 170, No. 2, pp. 247-256, (Aug. 15, 1998).
International Search Report, (Jun. 2005).
McPhillips et al., Characterisation of the glass transition of HPMC using modulated temperature differential scanning calorimetry, International Journal of Pharmaceutics 180 pp. 83-90 (1999).
Verreck et al., Characterization of solid dispersions of itraconazole and hydroxypropylmethylcellulose prepared by melt extrusion—part I, International Journal of Pharmaceutics 251, pp. 165-174 (2003).

* cited by examiner

*Primary Examiner* — Carlos Azpuru
*Assistant Examiner* — Casey Hagopian
(74) *Attorney, Agent, or Firm* — Carmella A. O'Gorman

(57) ABSTRACT

The present invention provides processes for making and forms of solid dispersions of pharmaceutical active ingredients.

5 Claims, No Drawings

PHARMACEUTICAL FORMULATION

The present invention provides processes for making and forms of solid dispersions of pharmaceutical active ingredients.

Substances that are selected for drug development based on their in vitro pharmaceutical activity comprise active substances which may have solubility or dissolution concerns in aqueous media and in vivo. The solubility of drug development compounds in aqueous medium is often determinative of whether the compounds will eventually be useful as drugs. Relatively insoluble compounds, for example those compounds which have a solubility in water of less than 200 µg/ml, e.g. 100 µg/ml, which show promising pharmaceutical activity, present a significant challenge to the development of pharmaceuticals, particularly oral dosage form pharmaceuticals.

Several factors can contribute to inadequate solubility of a pharmaceutical active substance, including, for example, hydrophobic functional groups on the exterior of the active substance molecules, non-ionizable nature of the molecules, and crystal structure. With some insoluble compounds, one can mix them with water soluble polymers to enhance dissolution and solubility in an aqueous medium. Additionally, the modification of crystal structure from a crystalline state to an amorphous state offers an opportunity to increase aqueous media solubility while leaving pharmaceutical activity intact. The reduction in order from crystalline to amorphous state reduces the energy required for dissolution and solvation of the active substance in the aqueous medium.

One of the methods employed to enhance the solubility of such compounds in drug formulations is to make homogeneous solid dispersions of insoluble pharmaceutical active substances that are miscible with high molecular weight water soluble polymeric matrices, such as, for example, polyvinylpyrrolidone (PVP) and hydroxypropylmethylcellulose (HPMC). (Improving drug solubility for oral delivery using solid dispersions. C. Leuner and J. Dressman. Eur. J. Pharmaceutics and Biopharmaceutics 50 (2000) 47-60.)

The water soluble polymer excipients act as a solubility bridge between the insoluble pharmacologically active compound and an aqueous medium. Solid dispersion technology typically combines pharmaceutical active substances that are mixed with liquefied water soluble polymers in order to stabilize pharmaceutical actives in their amorphous state. Increased dissolution and/or solubility of the active compounds can be achieved if amorphous forms of the compounds are dispersed with the liquefied water soluble polymers. With the proper choice of polymers it is possible to increase the solubility of drug substance as well.

The liquefied polymers can dissolve the active compound and grinding, stirring, or agitating the mixture can promote a molecular dispersion of the active compound in the polymer. Once the liquefied polymer and dissolved active compound are dispersed at a near molecular level distribution, the mix is dried or solidified to create a solid dispersion. The solid dispersion maintains the even molecular distribution and thus captures the active compound in what has been termed a solid solution with the water soluble polymer. The solid dispersion may then be finely ground and milled to create oral dosage drug forms containing the solid dispersion.

Molecular solid dispersions may be formed of active ingredients in viscous high molecular weight polymers such as HPMC and PVP. Such high molecular weight polymers are desirable for solid dispersions because they greatly inhibit crystallization of an amorphous active substance, enhance physical stability of the dispersion upon storage, and enhance dissolution profiles which lead to better in vivo bioavailability. However, creating such dispersions of active substances with the polymers typically requires the use of solvents or high temperatures or additional plasticizers to bring both or either of the components to a liquefied state. All of these methods may have drawbacks. Solid dispersions composed of polymers with higher molecular weights polymers (PVPK-39 and PVPK-90) compared to the lower molecular weights (PVPK-15 and PVPK-12) or higher glass transition temperatures have been shown to be more effective at inhibiting the crystallization of active ingredients. (Crystallization Inhibition in Solid Dispersions of MK-0591 and Poly(vinylpyrrolidone) Polymers. K. Khougaz and S. D. Clas. J. Pharmaceut. Sci., 89:10, October 2000.) Often improved wetting and thereby improved dissolution rate are afforded by a solid dispersion in polymers such as PVP. However, these polymers are usually demonstrated to have only limited application for the preparation of solid dispersions by the hot melt method and are particularly suitable for the preparation of solid dispersions by the solvent method. (Improving drug solubility for oral delivery using solid dispersions. C. Leuner and J. Dressman. Eur. J. Pharmaceutics and Biopharmaceutics 50 (2000) 47-60.) In fact, the chemical instability of PVP to heat and its high melting point (probably decomposing before melting), usually necessitates that the drug-PVP solid dispersions can only be prepared by the solvent method. (Pharmaceutical Applications of Solid Dispersion Systems. W. Chiou and S. Riegelman. J. Pharmaceut. Sci., 60:9, September 1971.)

The polymers which are used for solid dispersions often are liquefied at elevated temperatures. However, high temperatures can cause thermal degradation of either or both of active and excipient components and may present significant stability problems. The polymers, especially those with high molecular weights, for example HPMC and PVP, often may not melt at elevated temperatures readily but instead degrade before, during, or immediately after melting thus preventing the creation of optimal solid dispersion. Even at relatively lower temperatures, mechanical considerations or limitations prevent achievement of uniform and complete dispersion of the components.

Because of these limitations, the solvent method became more popular in the 1970s and 1980s. According to the solvent method, the polymers are liquefied by dissolution in organic solvents. However, organic solvents are usually undesirable due to environmental and/or economic considerations. Solid dispersions formed through the solvent method require evaporation and collection of expensive and hazardous spent solvents. The solvents are removed later from a drug product in time consuming and expensive processes. Complete evaporation of all solvent from the dispersion is often difficult to achieve and the rate at which solvent is evaporated in order to solidify the heterogeneous solution of liquefied active substance and polymer may allow some of the active substance to return to a crystalline state. In addition, appropriate solvents that solubilize both the active substance and the polymer may not always exist, or may require the use of unreasonably large amounts. Further, the solvents approved for such use are limited in number due to toxicity and environmental considerations. The ecological and subsequent economic problems associated with the use of organic polymers began to make solvent-based methods more and more problematic.

Plasticizers that are generally melted intimately with the active substance and the polymer to allow liquefaction at reduced temperatures are needed at high concentrations, for example greater than 40%, to be effective and therefore may compromise the physical stability, for example, increase crystallinity of the solid solutions. (Stability of Extruded 17β-Estradiol Solid Dispersion. S. Hulsmann, et al. Pharmaceutical Dev. and Technol., 6(2), 223-229 (2001).)

Further, additives such as plasticizers decrease the glass transition temperature of amorphous substances resulting in a promotion of crystallization and physical instability. (Crystallization Inhibition in Solid Dispersions of MK-0591 and Poly(vinylpyrrolidone) Polymers. K. Khougaz and S. D. Clas. J. Pharmaceutical Sci., 89:10, October 2000.)

These limitations often prevent the creation of solid dispersions where there are concerns regarding the solvent or the degradation of the active substances or excipient especially because a temperature at which both the excipient and the active will melt must be employed. Thus there is a need in the art of pharmaceutical development to provide a means for creating solid dispersion drug forms for insoluble compounds in water soluble polymers that have relatively high glass transition temperatures, for example $\geq 130°$ C., above which they may or may not liquefy, without using solvents and without thermal degradation and/or the need for high concentrations of plasticizers.

The inventors have surprisingly found that good results, avoiding solvent use or thermal degradation or additional plasticizing excipients, especially at the typically used high concentrations, may be achieved by creating solid dispersions for relatively insoluble pharmaceutical active substances, which have lower melting points or glass transition points than the water soluble polymers of choice, by first melting the active compound and then mixing a water soluble polymer with the melted active substance. According to the invention, the melt may be used as a plasticizer in order to effectively lower the glass transition temperature of the polymer and facilitate polymer liquefacation.

In addition the inventors have determined that polyols are particularly effective aids both as plasticizers and as lubricants in the processing of the softened amorphous active compounds with water soluble polymers, e.g. when using a melt extrusion device to make solid dispersion products of the invention.

The invention is particularly effective when employing the amorphous forms of the active substances which have even lower glass transition temperatures than their corresponding melting temperatures for the crystalline forms. This ensures that minimal thermal degradation of either the active substances or the polymers will occur and that both are miscible at molecular levels.

The description and examples of the present invention provided herein are illustrative and are not meant to limit the invention in any way.

Abbreviations:
TKA 731: (S)-1-(4-Oxo-1,4-dihydro-quinazolin-2-yl)-pyrrolidine-2-carboxylic acid[(S)-1-(benzyl-methyl-carbamoyl)-2-naphthalen-2-yl-ethyl]-methyl-amide
NKP608: (quinoline-4-carboxylic acid[trans-(2R,4S)-1-(3,5-bis-trifluormethyl-benzoyl)-2-(4-chloro-benzyl-piperidin-4-yl]-amide)
LAB687: (R)-[2,3-dihydro-5-[(6-methyl-4'-trifluoromethyl-[1,1'-biphenyl]-2yl)carbonylamino]-1H-inden-2-yl]-carbamic acid, methyl ester
ASM981: (1R,9S,12S,13R,14S,17R,18E,21S,23S,24R,25S,27R)-12-[(1E)-2-{(1R,3R,4S)-4-chloro-3-methoxycyclohexyl}-1-methylvinyl]-17-ethyl-1,14-dihydroxy-23,25-dimethoxy-13,19,21,27-tetramethyl-11,28-dioxa-4-azatricyclo[22.3.1.04,9]octacos-18-ene-2,3,10,16-tetraone
Fenofibrate: (2-[4-(4-Chlorobenzoyl)phenoxy]-2-methyl-propanoic acid)1-methylethyl ester
HPMC: hydroxypropylmethyl cellulose
PVP: polyvinylpyrrolidone
PVP K30: PVP of average molecular weight 30,000
PVP K90: PVP of average molecular weight 90,000
DSC: Differential Scanning Calorimetry
Tg: Glass Transition Point The invention provides the use of a drug substance, e.g. amorphous or crystalline drug substance, to solubilize polymers that are miscible with the active substance. The advantage that the new method offers in this case is that it allows the use of the higher molecular weight polymers without the need for solvents and for thermal methods without, or with minimal amounts of, additional excipients, e.g. plasticizers, that may compromise the stability of the dispersion, since the drug itself acts as a plasticizer. Higher molecular weight polymers, in comparison to those with a lower molecular weight, usually enhance the physical stability of the drug in the melt extrusion and gives a better bioavailability in vivo, all due to inhibition of crystallization of the drug.

As used herein the meaning of terms "pharmaceutical active agent", "active ingredient", "pharmacologically active compound", "active substance" or in some cases "drug substance" is to be understood as equivalent.

This invention also embodies a process to lower the temperature for dispersion using sugars and consequently any of the polyols to make it feasible to achieve dispersions within reasonable mechanical and thermal limitations. In one aspect of the invention it is envisioned to use polyols at concentrations of e.g. 0.2-50% by weight based on the total weight of the solid dispersion, depending on the viscosity limitations of the drug substance and polymers employed. A related invention is the use of hydrates, wherein the water of crystallization can be released during processing to facilitate uniform dispersion but the water would eventually be removed by evaporation with minimal residues in the mixture to adversely affect product stability either through a decrease in Tg or increase in hydrolytic instability. In one aspect of the invention a polymer may be selected such that the drug-polymer dispersion is phase separated from the polyol or polymer-polyol dispersion. In this instance, the Tg of the drug or drug-polymer dispersion may not be lowered by the use of polyols but the polyol may continue to prove effective in enhancing dispersion of drug-polymer dispersion well within mechanical limitations. This may be the case with the experimental TKA731-PVP-sorbitol system, where sorbitol, above its melting point is observed to be miscible with PVP but not with TKA731. Apart from lowering temperature for dispersion (avoids degradation of drug), reducing shear (reduced break down of polymer chains) and allowing low torque (higher throughput and below the mechanical limitations of the equipment) sorbitol is able to reduce the extent of degradation of drug substance by reducing the residence time of the mixture under high temperature. As sorbitols and many polyols are available as complex hydrates it may be possible to custom pick a hydrate, e.g. hemihydrate, monohydrate, sesquihydrate, dehydrate, heptahydrate or solvates, that will provide the right amount of water at the right temperature. As the rate of release of water tends to depend on particle size of the hydrates, it may be possible to customize the rate of water release from hydrates by customizing particle size of hydrates.

In preparing solid dispersions either where the drug dissolves in the polymer or where the polymer dissolves in the drug polyols can be of substantial use, especially in melt extrusion processes. Use of polyols may be of considerable use when use of polymers of increasingly higher molecular weight are needed or where the stability or the nature of the drug is such that low temperatures and high viscosities need to be dealt with.

In the past, liquids have been traditionally used to solve the problems with mechanical limitations and/or to deal with high viscosities, however efficient dispersion is a problem as sufficient time may not be available for it to exert its influence before the drug degrades. Use of hydrates as powder mixtures that allow for intimate mixing and processing by releasing water at particulate level allows for enhancement of the manufacturing process.

The preparations containing active ingredient can contain as matrix polymers. Mixtures of polymers may be used. Suitable active ingredients are all active ingredients which do not decompose under the conditions of melt extrusion.

Polyols had occasionally been used to generally enhance solubility of the drug and therefore reduce the levels of any solvents employed with a solvent-mediated process. However finding a solvent that can dissolve both the polymer and drug is often difficult and even optimal solvents, owing to solubility limitations, can be needed in enormous amounts.

The invention provides a process for preparing a solid dispersion pharmaceutical product wherein the product contains a pharmaceutical active ingredient and a polymer, e.g. pharmaceutically acceptable inactive polymer. Optionally, the polymer may be combined with one or more further polymer(s) or excipient(s), e.g. pharmaceutically acceptable inactive polymer(s) or excipient(s). This process, among its other benefits, enhances the dispersion of components and reduces the degradation of the polymers used and of the active substance. The process is performed through the steps of first liquefying or softening the pharmaceutical active ingredient, then adding the polymer, e.g. in combination with further excipients, to the liquefied or softened pharmaceutical active ingredient in order to produce a mixture of the liquefied or softened pharmaceutical active ingredient with the polymer, then allowing the liquefied or softened mixture to become liquefied or softened throughout, then allowing the mixture to form a molecular dispersion of pharmaceutical active ingredient and polymer, then solidifying the dispersion in order to create a solid dispersion.

It is contemplated that hydrophobic polymers may also be selected to be employed as the polymers in the invention in order to keep moisture/humidity away from water-sensitive drugs. Further, argon, helium or nitrogen may be used during processing to keep oxidation level down.

Another aspect of the invention allows for the additional steps of stirring or agitating the mixture of active ingredient and polymer in order to create a heterogeneous liquefied or softened even dispersion of pharmaceutical active ingredient and polymer.

The invention also allows that once a solid dispersion is formed using the process of the invention the solidified dispersion may be ground in order to create a solid dispersion powder or granulate.

One aspect of the invention allows that the process step of liquefaction or softening of pharmaceutical active ingredients may be achieved by heating the active ingredient to a temperature at or above its melting point or glass transition temperature, in order to melt the active ingredient. The elevated temperature is maintained during the addition, mixing, and dispersion of the polymer with the melted active ingredient in order to liquefy or soften the polymer.

The invention also provides for an optional step of rapidly cooling the melted dispersed ingredients of the pharmaceutical product to a temperature that is below the temperature required to melt the ingredients in order to solidify and thus capture the even mixture of active and inactive ingredients in the dispersion. In the cooling step, the temperature required to cool and solidify the dispersion is desirable when the temperature is below 40° C. and more desirable when the temperature is below 0° C. An even more desirable cooling temperature is below −50° C. The cooling step is performed rapidly in order to ensure that the mixture in the dispersion is maintained evenly heterogeneous, e.g. in form of an even molecular dispersion of heterogenous molecules, until it solidifies. It is desirable that the dispersion is brought to the temperature to solidify the dispersion in less than five minutes and more desirable that the solidification temperature be achieved in less than one minute. It is even more desirable that the dispersion be brought to the solidification temperature in under ten seconds and exceptionally desirable that the step be performed in less than one second.

The invention also allows for the additional step of using the pharmaceutical active ingredient which is in an amorphous state. By the term "amorphous" as used herein is meant a non-crystalline state, e.g. a non-ordered random solid system.

A further aspect of the invention provides that a melt extrusion device may be employed to create the molecular dispersion. It is contemplated that the melt extruder device may be incorporated into the process of the invention through the steps of injecting the solid or liquefied mixture into a melt extruder device and operating the melt extruder device at a temperature above the melting point or glass transition temperature of the active ingredient prior to allowing the mixture to form the molecular dispersion, and extruding said molecular dispersion from the tip of the melt extrusion device, prior to solidifying said dispersion.

It is contemplated and desirable that the melt extruder device which may be employed in the process of the invention is equipped with screw elements or paddles in order to efficiently mix the ingredients of the pharmaceutical product.

The invention allows that the amorphous pharmaceutical active ingredient may first be added to a melt extrusion device and heated to a temperature above its glass transition point in order to liquefy or soften it and also that the polymer and optionally further excipients are added to the liquefied pharmaceutical active ingredient in the melt extrusion device in order to more efficiently, and at a lower temperature, liquefy or soften the polymer and optionally further excipients and produce an even homogeneous mixture. The above can also be achieved by mixing the pharmaceutical active ingredient that is in an amorphous state uniformly with the polymer and optional further excipients in the solid state and adding them to a melt extrusion device heated to a temperature above the glass transition point of the active substance in order to liquefy or soften it and that in turn will result in dissolving/liquefying the excipients at a temperature lower than the glass transition temperature of the polymer and optional further excipients. In addition, a melt extruder equipped with screw elements or paddles may be used to process the amorphous or non-crystalline pharmaceutical active ingredient in the steps outlined above.

It is contemplated that the pharmaceutically acceptable inactive excipients or polymers used to create the pharmaceutical product in the process of the present invention may be selected from any pharmaceutically acceptable matrix or water soluble or partially water soluble polymers. Examples of excipients or polymers include any pharmaceutically acceptable inactive excipient or polymer e.g. melt-processable polymers, for example polyvinylpyrrolidone, copolymers of N-vinylpyrrolidone and vinyl acetate with up to 50% by weight of vinyl acetate, carboxyalkylcelluloses such as carboxymethylcelluloses, alkylcelluloses such as methylcellulose, hydroxyalkylcelluloses such as hydroxymethyl-, hydroxyethyl-, hydroxypropyl- and hydroxybutylcellulose, hydroxyalkylcelluloses such as hydroxyethylmethyl- and hydroxypropylmethylcellulose, or mixtures thereof.

Preferred polymers are polyvinylpyrrolidone (PVP) and hydroxypropylmethylcellulose (HPMC). According to the invention, mixtures of excipients or polymers may be used.

As used herein the term "inactive" means without any pharmacological effect.

In addition, the pharmaceutical active substance used to create the pharmaceutical product in the process of the invention may be selected from the following group: central nervous system active agents, peripheral nervous system active agents, vascular active agents, dermatologic active agents, gastrointestinal active agents, oncologic and anti-tumor agents, bone active agents, hormonal active agents, immune system active agents, anti-infective agents, respiratory active agents, neuro-muscular active agents, and anti-diabetic agents.

The process of the invention has also been found to be particularly advantageous to process the pharmaceutical active agents TKA 731, NKP608, LAB687, ASM981, and fenofibrate in a solid dispersion.

It is an aspect of the invention to provide that the process for preparing a solid dispersion pharmaceutical product may be carried out in an extrusion device to combine a pharmaceutical active ingredient and a polymer, e.g. in combination with further excipients, with a polyol having water of hydration for reduction of torque. The addition of the polyol hydrates serves to lower the viscosity and friction associated with melt extrusion and maintain low or no degradation of the active or inactive ingredients. The process using the polyol is carried out by
- combining the pharmaceutical active ingredient, the polymer, e.g. in combination with further excipients, and the polyol having a water of hydration to create a lubricated mixture,
- liquefying or softening the lubricated mixture,
- injecting said liquefied or softened mixture into an extruder device,
- then forcing said liquefied or softened lubricated mixture through the extruder device in order to form a lubricated molecular dispersion of the pharmaceutical active ingredient, the polymer, e.g. in combination with further excipients, and the polyol,
- extruding said lubricated molecular dispersion from the tip of the extruder,
- then solidifying said lubricated molecular dispersion in order to create a solid dispersion.

The melt extrusion process of the invention may also be carried out in an extruder device which is equipped with screw elements or paddles.

An additional aspect of the invention includes using a polyol which, for example, is a six carbon sugar or six carbon sugar alcohol in the melt extrusion process wherein the polyol has water of hydration. Examples of polyols include sorbitol, mannitol, sucrose, polyethylene glycol or propylene glycol. A preferred polyol is a six carbon sugar or six carbon sugar alcohol, e.g. sorbitol. The polyols may be selected from any pharmaceutically acceptable excipients based on the temperatures at which the polyol hydrates will release water and convert to lesser or partial hydrates or anhydrous form. Additionally, unique complexing polyols such as cyclodextrins may be employed in the invention. Where a drug is immiscible with a polymer, a drug complexed with cyclodextrin may be used to increase the choice of the polymers or increase the amount of drug that may be loaded in the polymer without phase separation or risk or recrystallization.

A further aspect of the invention allows for the use of a polyol to aid melt extrusion processing of the pharmaceutical active and inactive ingredients into a solid dispersion product. Such use may be achieved by first heating the active ingredient to a temperature at or above its melting point, in order to melt the active ingredient, and then adding the polymer, optionally further excipients, and polyol to the melted active ingredient in the extrusion device in order to produce the lubricated mixture and liquefy or soften the polymer and polyol. In this variation, the temperature used to heat and melt the ingredients is maintained during the addition, mixing, and dispersion of the polymer and polyol with the melted active ingredient in order to liquefy or soften the pharmaceutically acceptable polymer and polyol.

In one aspect the invention provides that the solid dispersion process of the invention which employs melt extrusion of the active and inactive ingredients and polyol, includes the pharmaceutical active ingredient in an amorphous state. An amorphous pharmaceutical active ingredient is used to further reduce the melting temperature of the mixture and also to employ a more soluble form of the pharmaceutical active ingredient in the solid dispersion product.

Another aspect of the invention provides that the melt extrusion process for making the solid dispersion may be carried out by first adding the amorphous pharmaceutical active ingredient to a melt extrusion device and heating the active ingredient to a temperature above its glass transition point in order to liquefy or soften it and then adding the polymer and optionally further excipients to the melted active ingredient in the melt extrusion device in order to liquefy or soften the polymer and optional excipients and polyol. A further aspect of the invention allows that the melt extruder used may be equipped with screw elements or paddles in order to efficiently mix and melt the ingredients.

The present invention provides that the melt extrusion process of creating the solid dispersion from a pharmaceutical active ingredient, polymer, optional further excipients, and the polyol includes that the pharmaceutical excipients or polymers may be selected from any pharmaceutically acceptable matrix or water soluble polymers. According to the invention, mixtures of excipients or polymers may be used. In addition, the pharmaceutical active substance may be selected from the following group: central nervous system active agents, peripheral nervous system active agents, vascular active agents, dermatologic active agents, gastrointestinal active agents, oncologic and anti-tumor agents, bone active agents, hormonal active agents, anti-infective agents, respiratory active agents, neuro-muscular active agents, and anti-diabetic agents.

The melt extrusion process of the invention is particularly useful for creating solid dispersions of the following pharmaceutical active agents TKA731, NKP608, LAB687, ASM981, and fenofibrate.

An aspect of the invention provides a product comprising a pharmaceutical solid dispersion having no residual organic solvent, which organic solvent is in liquid phase at room temperature, containing a pharmaceutical active ingredient which has a solubility of less than 200 µg/ml, e.g. 100 µm/ml, in an aqueous medium, which is defined as a medium wherein the predominant liquid component is water, and a water soluble or partially water soluble polymer, e.g. pharmaceutically acceptable inactive polymer, optionally containing one or more further excipient(s), is formed by the process of the present invention comprising the steps of
- first liquefying or softening the pharmaceutical active ingredient, then adding the polymer and optionally further excipients to the liquefied or softened pharmaceutical active ingredient in order to produce a mixture of the liquefied or softened pharmaceutical active ingredient with the polymer and optional further excipients, alternatively to the above two points the pharmaceutical active ingredient may be mixed with the polymer and optionally further excipients uniformly in the solid state and subjecting them to the process. The pharmaceutical active ingredient, e.g. having a lower melting point or glass transition temperature than the inactive excipients and polymers, will liquefy or soften first and will start dissolving/liquefying the inactive polymer and optional further excipients, then allowing said liquefied or softened mixture to become liquefied or softened throughout, then allowing said mixture to form a molecular or supramolecular dispersion of pharmaceutical active ingredient and polymer and optional further excipients, and then solidifying said dispersion in order to create a solid dispersion.

Another aspect of the invention provides that the product formed by the aforementioned process contains the pharmaceutical active ingredient which is in an amorphous state. In a further aspect, the present invention allows that the product formed by the present process further contains a polyol, and that the polyol may be a six-membered sugar or sugar alcohol, e.g. sorbitol.

EXAMPLE 1

A solid dispersion is prepared using melt extrusion that contains 30% TKA731 and PVPK-30 (ISP Technologies, Wayne, N.J.) showing one single glass transition by Differential Scanning Calorimetry indicating a solid solution formed by this process is similar to the dispersion prepared using solvent method. The glass transition temperature of the extrusion is 137.20° C., with an onset of 130.0° C. which is very similar to the dispersion prepared by the solvent method where the glass transition temperature is 139.9° C., with an onset of 131.9° C.

The glass transition temperature of PVPK-30 determined by DSC is 175° C. Attempts to first liquefy the PVPK-30, by heating around and above 175° C. and observing the sample by light microscope shows no liquefaction even upon heating up to 240° C. Additionally, the polymer color changes from white to orange/brown color indicating degradation.

The glass transition temperature of amorphous TKA731 (drug substance) determined by DSC is 94.5° C. Inspection with hot stage light microscope shows that the drug substance starts turning into a liquid at temperatures above 95° C. and becomes totally liquefied with continued heating up to 140° C. This temperature is still below the glass transition temperature of the polymer and below the melting temperature of the active substance in its crystalline form (175.4° C.). Inspection by hot stage light microscope shows that PVPK-30 (polymer) added to the liquefied TKA731, at temperatures 95° C. starts dissolving in the drug at this temperature which is far below the glass transition temperature of the polymer (175° C.) and continues to do so as temperature is increased until everything turns into liquid. Furthermore, a mixture of 30% TKA731 and PVPK-30 mixed in the solid state and then inspected/heated by hot stage light microscope shows liquefaction at temperatures above 95° C., which is the glass transition temperature of the amorphous form of TKA731 active substance. Also the plasticization effect of the drug on the polymer is exhibited by reducing the glass transition temperature of the polymer and this reduction increases as the drug load increases (See Table 1).

Solid dispersions prepared by the process described herein, starting with the amorphous form of TKA731, results in the formation of real solid solution where the polymer and the drug are molecularly and homogeneously mixed, as shown by one single Tg by DSC. Additionally, the solid dispersions are totally amorphous, as exhibited by the diffused halo and lack of peaks in the X-ray diffraction patterns, and the dispersions show no thermal degradation as proved by HPLC analysis (See Table 2).

TABLE 1

Solid Dispersion formed by the process described herein

| Drug load | Polymer content (PVPK-30) | Glass transition temperature (° C.)/DSC | X-ray analysis | HPLC analysis |
|---|---|---|---|---|
| 100% | 0% | 94.5 | amorphous | No degradation |
| 40% | 60% | 135.1 (single)* | amorphous | No degradation |
| 30% | 70% | 139.8 (single)* | amorphous | No degradation |
| 20% | 80% | 147.7 (single)* | amorphous | No degradation |
| 0% | 100% | 175 | amorphous | No degradation |

*A single glass transition temperature indicates complete miscibility between the drug substance and the polymer i.e. formation of amorphous solid solution.

The melting point of TKA731 active substance in its crystalline form as determined by DSC is 175.4° C. Analysis of the drug substance after it melts by HPLC shows chemical thermal degradation varying between 10% and 20%.

Preparing the solid dispersions starting with the amorphous form and applying the process described above results in the ability to use processing temperatures that result in the formation of solid dispersions exhibiting no thermal degradation as seen in analysis by HPLC (see Tables 2 and 3).

TABLE 2

Solid dispersions formed using the process described herein starting with the amorphous form of the drug

| Physical state of TKA731 | Melting point (° C.) | Glass transition temperature (° C.) | X-ray analysis after Solidification | HPLC analysis |
|---|---|---|---|---|
| Crystalline drug | 175 | * | amorphous | 20% degradation |
| Amorphous drug | **— | 94.5 | amorphous | No degradation |

*No Glass Transition Temperature for crystalline form.
**No Melting Point for amorphous form.

EXAMPLE 2

Solid dispersions are prepared using melt extrusion that contains 30% TKA731 and PVPK-30 (ISP Technologies, Wayne, N.J.), the dispersions additionally contain sorbitol (EM Industries, Darmstadt, Germany) in concentrations of 5% or 10% or do not have additional sorbitol (control) by weight. The dispersions show one single glass transition by Differential Scanning Calorimetry indicating a solid solution formed by this process is similar to the dispersion prepared using solvent method.

The plasticization effect of sorbitol (EM Industries, Darmstadt, Germany), on the drug/polymer mixture is exhibited by the lack of degradation at a processing temperature of 170° C. (see Table 3)

TABLE 3

Solid dispersions formed using the process described herein starting with the amorphous form of the drug, and utilizing an additional polyol plasticizer

| Amorphous drug load | Polymer content (PVPK-30) Tg = 175° C. | Plasticizer concentration (sorbitol) | Processing temperature (° C.)[2] | X-ray analysis | HPLC analysis |
|---|---|---|---|---|---|
| 20% | 70% | 10%[1] | 170 | amorphous | No degradation |
| 30% | 65% | 5%[1]  | 170 | amorphous | No degradation |
| 40% | 60% | 0%     | 170 | amorphous | No degradation |

[1] Plasticizer concentrations lower than the above values might also be feasible
[2] Lower processing temperatures might be feasible The amorphous form of other drugs (LAB687, NKP608 and fenofibrate) inspected by DSC and hot stage light microscope showed that the drug turns into a liquid form far below the melting point of its crystalline counterpart and far below the glass transition temperature of the polymer (PVP and/or HPMC). The polymer (PVP and/or HPMC) when added in a solid form to the liquefied drug above the glass transition temperature of the drug starts to dissolve in the drug and continued to do so upon heating. Inspection of solid dispersions of these compounds prepared with PVPK-30 and/or HPMC by DSC showed that the drug in its amorphous form plasticizes and reduces the Tg of the polymer similar to what was observed for TKA731.

The invention claimed is:

1. A process for preparing a pharmaceutical product comprising a pharmaceutical active ingredient and a water soluble or partially water soluble polymer comprising the steps of
liquefying or softening an amorphous pharmaceutical active ingredient by heating the pharmaceutical active ingredient to a temperature at or above its glass transition temperature;
adding the water soluble or partially water soluble polymer to the liquefied or softened pharmaceutical active ingredient at a temperature below the glass transition temperature of the water soluble or partially water soluble polymer to produce a mixture;
allowing the mixture to become liquefied throughout;
allowing said mixture to form a molecular dispersion of pharmaceutical active ingredient and polymer; and
solidifying said dispersion;
wherein the amorphous pharmaceutical active ingredient has a solubility in water of less than 200 μg/ml and a glass transition temperature of less than the water soluble or partially water soluble polymer.

2. The process of claim 1 further comprising stirring or agitating said mixture until homogeneous.

3. The process of claim 1 further comprising grinding the dispersion into a powder or granulate.

4. The process of claim 1, wherein said solidifying is rapid cooling.

5. The process of claim 1, further comprising the steps of injecting the liquefied or softened mixture into a melt extruder device and operating the melt extruder device at a temperature above the melting point or glass transition temperature of the pharmaceutical active ingredient prior; and
extruding the molecular dispersion prior to solidifying said dispersion.

* * * * *